United States Patent
Aubert et al.

(10) Patent No.: US 10,376,207 B2
(45) Date of Patent: Aug. 13, 2019

(54) CALCULATING A CURRENT CIRCADIAN RHYTHM OF A PERSON

(71) Applicant: KONINKLIJKE PHILIPS N.V., Eindhoven (NL)

(72) Inventors: Xavier Louis Marie Antoine Aubert, Brussels (BE); Henning Maass, Waalre (NL); Guido Josef Muesch, Erkelenz (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 15/036,160

(22) PCT Filed: Dec. 1, 2014

(86) PCT No.: PCT/EP2014/076061
§ 371 (c)(1),
(2) Date: May 12, 2016

(87) PCT Pub. No.: WO2015/082382
PCT Pub. Date: Jun. 11, 2015

(65) Prior Publication Data
US 2017/0007178 A1    Jan. 12, 2017

(30) Foreign Application Priority Data
Dec. 2, 2013   (EP) .................................. 13195320

(51) Int. Cl.
*G06F 19/00* (2018.01)
*A61B 5/00* (2006.01)
(Continued)

(52) U.S. Cl.
CPC ........ *A61B 5/4857* (2013.01); *A61B 5/02055* (2013.01); *A61B 5/1118* (2013.01);
(Continued)

(58) Field of Classification Search
CPC .................. G06F 19/3437; G06F 19/00; A61B 2560/0242; A61B 2562/0219;
(Continued)

(56) References Cited

U.S. PATENT DOCUMENTS 5,704,017 A * 12/1997 Heckerman ............ G06Q 30/02
                                                            706/12
5,805,447 A *  9/1998 Teng .................. G05B 13/0235
                                                            700/28
(Continued)

FOREIGN PATENT DOCUMENTS

EP       2656782 A1    10/2013
WO    2012056342 A2    10/2011

OTHER PUBLICATIONS

Shanmugam et al, "Disruption of Circadian Rhythm Increases the Risk of Cancer, Metbolic Syndrome and Cardiovascular Disease".
(Continued)

*Primary Examiner* — Caridad Everhart (57) ABSTRACT

The invention relates to an apparatus (100) and a method for generating a model output x(ti) describing a circadian rhythm of a person (P) at a time ti. In a preferred embodiment, a light sensor providing the photic exposure (L(ti)) and an activity signal (A(ti)) indicating the current level of activity of the person (P) at the time ti based on motion measurements (via an accelerometer) are used to calculate a wakefulness variable (σ) that indicates if the person (P) is awake or sleeping. The wakefulness variable is then used to determine a driving term (N(t)) for a driven oscillator model (135) which simulates the model output x(t) under the joint influence of light and activity.

15 Claims, 2 Drawing Sheets

(51) Int. Cl.
*A61B 5/0205* (2006.01)
*A61B 5/11* (2006.01)
*G16H 50/50* (2018.01)
*A61B 5/021* (2006.01)
*A61B 5/024* (2006.01)

(52) U.S. Cl.
CPC ............ *A61B 5/4809* (2013.01); *A61B 5/681* (2013.01); *A61B 5/7225* (2013.01); *A61B 5/7264* (2013.01); *G06F 19/00* (2013.01); *G16H 50/50* (2018.01); *A61B 5/021* (2013.01); *A61B 5/024* (2013.01); *A61B 2560/0242* (2013.01); *A61B 2562/0219* (2013.01)

(58) Field of Classification Search
CPC ....... A61B 5/681; A61B 5/4857; A61B 5/021; A61B 5/02055; A61B 5/024; A61B 5/1118; A61B 5/7225; A61B 5/4809; A61B 5/7264; G16H 50/50
See application file for complete search history.

(56) References Cited

U.S. PATENT DOCUMENTS

| | | | |
|---|---|---|---|
| 2002/0005784 | A1 | 1/2002 | Balkin et al. |
| 2005/0001512 | A1 | 1/2005 | Moguchi et al. |
| 2006/0224047 | A1 | 10/2006 | Suzuki et al. |
| 2009/0207028 | A1* | 8/2009 | Kubey .................. A61B 3/113 340/575 |
| 2010/0138379 | A1 | 6/2010 | Mott et al. |
| 2013/0218030 | A1 | 8/2013 | Barroso et al. |
| 2015/0186594 | A1* | 7/2015 | Zhang ................ G06F 19/3437 703/2 |
| 2017/0095665 | A1* | 4/2017 | Demmer ............. A61N 1/3621 |

OTHER PUBLICATIONS

Whitmire et al, "Risk of Performance Errors Due to Sleep Loss, Circadian Desynchronizaiton, Fatigue, and Work Overload", Human Research Program Requirements Document, HRP-47052, Rev. C, 2009, pp. 85-116.
Terman et al, "A Controlled Trial of Timed Bright Light and Negative Air Ionization for Treatment of Winter Depression", Archive Gen. Psychiatry, vol. 55, 1998, pp. 875-882.
Hilaire et al, "Addition of a Non-Photic Component to a Light-Based Mathematical Model of the Human Circadian Pacemaker", Journal of Theoretical Biology, vol. 247, 2007, pp. 583-599.
Brown et al,"Actigraphy: A Means of Assessing Circadian Patterns in Human Activity", The Journal of Biological and Medical Rhythm Research, vol. 7, No. 2, 1990, Ages 125-133.
Kronauer et al, "Quantifying Human Circadian Pacemaker Response to Brief, Extended, and Repeated Light Stiumul Over the Phototopic Range", Journal of Biological Rhythms, vol. 14, No. 6, 1999, pp. 501-515.
Ancoli-Israel et al, "The Role of Actigraphy in the Study of Sleep and Circadian Rhythms", Sleep, vol. 26, No. 3, 2003, pp. 342-3922345.
Coughlin, "Characterization of Light Sensor Performance for Three Models of Actiwatch Actiwatch-64, Actiwtch 2 and Actiwatch Spectrum Actiwatch-L", Jan. 2008, pp. 1-4.
Adamec et al, "Statistical Characterization of Actigraphy Data During Sleep and Wakefulness States", 32nd Annual International Conference of the IEEE EMBS, Buennos Aires, Argentina, 2010, pp. 2342-.

* cited by examiner

CALCULATING A CURRENT CIRCADIAN RHYTHM OF A PERSON

CROSS-REFERENCE TO PRIOR APPLICATIONS

This application is the U.S. National Phase application under 35 U.S.C. § 371 of International Application Serial No. PCT/EP2014/076061, filed on Dec. 1, 2014, which claims the benefit of European Application Serial No. 13195320.0, filed on Dec. 2, 2013. These applications are hereby incorporated by reference herein.

FIELD OF THE INVENTION

The invention relates to a method and an apparatus for estimating a model output describing a circadian rhythm of a person.

BACKGROUND OF THE INVENTION

Since the existence and importance of circadian rhythms in human beings and animals is known, products have been developed that try to use this knowledge. The US 2005/0015122 discloses for example methods for controllably adjusting the circadian pacemaker cycle of a subject using light through application of model-based predictive control techniques.

EP 2 656 782 A1 discloses a device consisting of at least one body position and activity sensor, at least one peripheral temperature sensor and at least one light sensor, configured to provide information on the circadian system status and the sleep-wake status of an individual based on the data obtained from said sensors. It can be placed on the wrist of the subject, or on the subject's arm. The device may also include a blood pressure sensor. This device may be used in general studies of the human circadian system and, more specifically, for the study of sleep-wake and blood pressure rhythms.

WO 2012/056342 A2 discloses a method for determining a feature of the circadian rhythm of the subject, comprising measuring a first input signal indicating a cardiac function of the subject, measuring at least one second input signal indicating the activity of the subject, combining the first input signal and the second input signal to a periodic output signal representing the circadian rhythm of the subject, and determining at least one feature of this periodic output signal.

The article "Addition of a non-photic component to a light-based mathematical model of the Human Circadian Pacemaker" by St. Hilaire M. A. et. al., Journal of Theoretical Biology, vol. 247, pp. 583-599 (2007) discloses a modified light-based circadian mathematical model to reflect evidence from studies that the sleep-wake cycle and/or associated behaviors have a non-photic effect on the circadian pacemaker. The sleep-wake cycle and its associated behaviors provides a non-photic drive on the circadian pacemaker that acts both independently and concomitantly with light stimuli.

The article "Actigraphy: A Means of Assessing Circadian Patterns in Human Activity" Brown A. C. et. al., Chronobiology International, vol. 7, no. 2, pp. 125-133 (1990) discloses the continuous monitoring of twenty-three diurnally active (0705-2333), healthy persons between 22 and 54 yrs of age and without history of sleep abnormality for 120 consecutive hr (five days) by wrist actigraphy. Circadian rhythms of high amplitude were detected by cosinor analysis for each participant and for the groups of 10 males and 13 females with the average span of heightened activity timed between ~1330 and 1605. The circadian peak-trough difference in wrist movement was marked, equaling approximately 75% of the 24-hr mean level. In 19 of 23 participants, the 24•hr mean of wrist activity varied between 140-180 movements/min, with four persons exhibiting lesser means of 110-140 movements/min. With respect to the daytime span of activity, the mean wrist movement of individual participants ranged from 155-265 movements/min, with the majority (20/23) varying between 185-245 movements/min. During nocturnal sleep the mean wrist activity level was quite low, varying between individuals from 5 to 25 movements/min for 21 of 23 persons. Wrist actigraphy proved to be well-accepted and was a most reliable means of monitoring aspects of body movement during activity and sleep in ambulatory persons adhering to usual life habits and pursuits.

SUMMARY OF THE INVENTION

Based on this situation, it was an objective of the present invention to provide means that allow for an improved estimation of the circadian rhythm of a person.

This objective is addressed by an apparatus according to claim 1, a system according to claim 9, a method according to claim 12, and a computer program according to claim 15.

In a first aspect of the invention, there is provided an apparatus for generating a model output at a first time describing a circadian rhythm of a person, said apparatus comprising: an input module for receiving an activity signal indicative of a current level of activity of the person at the first time based on activity level measurements; a classification module for generating a wakefulness signal at the first time, the wakefulness signal being indicative of the person being awake or asleep at the first time, wherein said a classification module is preferably adapted for generating said wakefulness signal based on the received activity signal; a first calculation module for determining a non-photic driving term at the first time, the non-photic driving term representing a non-photic influence on the circadian rhythm, wherein the first calculation module is configured to determine the non-photic driving term based on the wakefulness signal; and a simulation module for calculating in real time the current model output at the first time based on at least the non-photic driving term.

An embodiment of the claimed invention may specifically provide a continuous epoch-by-epoch update of the internal time evolution, where an epoch corresponds to a given period in time.

In an embodiment, the input module is further configured for receiving a lighting level signal indicative of a lighting level at the first time at a location of the person; and the classification module is further configured for generating the wakefulness signal based on the received lighting level signal and/or based on the received activity signal.

In a further embodiment, the apparatus further comprises a second calculation module for determining a photic driving term, the photic driving term representing a photic influence on the circadian rhythm, wherein the second calculation module is configured to determine the photic driving term from the received lighting level signal; wherein the simulation module is further arranged for calculating in real time the current model output at the first time based on the non-photic driving term and on the photic driving term.

In a further embodiment, the classification module is further arranged to generate the wakefulness signal at the first time based on one more recent activity signals and/or based on one or more recent lighting level signals, wherein the one or more recent activity signals correspond to one or more activity signals taken prior in time to the first time, wherein the one or more recent lighting level signals correspond to one or more lighting level signals taken prior in time to the first time.

In a further embodiment, the classification module is further arranged for receiving at least one threshold of the person, wherein the classification module is further configured to compare the threshold to a weighted sum of recent activity signals and/or of recent lighting level signals, wherein the classification module is further configured to generate a personal baseline of activity or lighting level for the person.

In a further embodiment, a classifier score $RnD_{score}(I)$ is computed at a current epoch according to $$RnD_{score}(I) = w1 \cdot \sum_{i=0}^{n-1} \alpha(i) * A(t_{I-i}) + w2 \cdot \sum_{i=0}^{p-1} \beta(i) * L(t_{I-i})$$

where w1 and w2 correspond to predetermined first and second weights, where w1≥0 and w2≥0, where $\alpha(i)$ correspond to predetermined non-photic coefficients, and where $\beta(i)$ correspond to predetermined photic coefficients, and where the current epoch corresponds to a current period in time.

In a further embodiment, the current model output is calculated based on a driven van-der-Pol oscillator model.

In a further embodiment, the non-photic driving term is proportional to a gain factor, and a time at which a minimum core body temperature of the person occurs is determined as the time for which a minimum current output signal is generated plus an offset, wherein the offset depends on the gain factor, wherein the offset is preferably expressed as a−b·ρ, where a and b are constant, and where ρ corresponds to the gain factor.

In a further aspect, there is provided a system for generating a model output at a first time describing a circadian rhythm of a person, said system comprising: at least one sensor for determining an activity signal at a first time indicating the activity of the person at the first time, and the above-described apparatus.

In a further embodiment, the at least one sensor is an acceleration sensor or a physiological parameter sensor, wherein the physiological parameter sensor is preferably a heart rate sensor, a blood pressure sensor, or a body temperature sensor.

In a further embodiment, the system further comprises a sensor for determining a lighting level signal at the position of the person at the first time.

In a further aspect, there is provided a method for generating a model output at a first time, the model output describing a circadian rhythm of a person, said method comprising the following steps: receiving an activity signal indicating a current level of activity of the person at the first time based on activity level measurements; classifying the received activity signal, such that a wakefulness signal is generated, the wakefulness signal being indicative of the person being awake or asleep at the first time; determining a non-photic driving term that represents a non-photic influence on the circadian rhythm, wherein the non-photic driving term is determined based on the wakefulness signal; and calculating in real time the current model output based on at least the non-photic driving term.

In an embodiment, the method further comprises the steps of: receiving a lighting level signal indicating of a lighting level at a location of the person at the first time; determining a photic driving term from the lighting level signal; and calculating in real time the current model output at the first time based on the non-photic driving term and on the photic driving term.

In a further embodiment, the wakefulness signal is calculated by; (i) calculating a score as a weighted sum of current and past activity signals and/or of current and past lighting level signals; and (ii) comparing the score to at least one threshold.

In a further aspect, there is provided a computer program comprising program code means for causing, when executed, an apparatus for generating a model output describing a circadian rhythm of a person as described above, to carry out the steps of the method as defined above.

According to a further aspect, there is provided an apparatus for estimating a model output x(t) describing the circadian rhythm of a person, said apparatus comprising the following components:

A first module for receiving a signal that indicates the current level of activity of the person based on activity level measurements. Said module will be called "input module" and said signal will be called "activity signal" in the following.

A second module, called "simulation module" in the following, for calculating a current model output x(t) taking said activity signal into account.

The apparatus may particularly be realized by or comprise dedicated electronic hardware, digital data processing hardware with associated software, or a mixture of both. The modules of the apparatus may be realized by different hardware components. Additionally or alternatively, the modules may be realized by different (sub-)routines of a computer program that may optionally run on the same hardware.

According to a further aspect, an embodiment of the invention relates to a method for estimating a model output x(t) describing the circadian rhythm of a person, said method comprising the following steps:

Receiving an activity signal that indicates the current level of activity of the person based on activity level measurements.

Calculating a current model output x(t) taking said activity signal into account.

The "model output" x(t) may in general be any kind of one- or multi-dimensional signal or value that is suited to describe the current state of the circadian rhythm of the person. It may encode its information for example as analogue or digital value(s), particularly a value oscillating between an upper and a lower limit corresponding to states of maximum and minimum activity of the person, respectively.

The "activity signal" may be any kind of signal, for example a voltage or an electrical current representing digital numbers and/or analog values. The activity signal shall preferably be based on "non-photic" activity level measurements, which means that it does not directly represent or depend on the lighting level around the person (as said lighting level usually affects the activity of the person, there may typically be some indirect dependence). In general, light is usually the most influential stimulus ("photic" by definition) onto the human circadian system whereas other non-photic stimuli exert a secondary influence (e.g.

external temperature, eating or physical movements). The activity level measurements may for example be executed with the help of an accelerometer sensor that provides an indication about movements of the person.

It should be noted that the term "current" indicates that measurements and calculations are made at some specific point in time (or, more precisely, during some small time interval). In particular, the most recent ("current") activity signal is taken into account for determining the current model output x(t).

The apparatus and the method are based on the same inventive concept, i.e. the exploitation of non-photic activity signals in the calculation of the current model output. Explanations provided for the apparatus are therefore analogously valid for the method and vice versa. The apparatus and the method have the advantage that an improved real-time estimation of the circadian rhythm is possible because a non-photic activity signal is taken into account which is up-to-date without requiring data of the future.

In the following, various preferred embodiments will be described that can be realized both in connection with the apparatus and the method (even if they are explained only for one of the apparatus or the method).

The activity signal may comprise any information that is related to the activity of a person without being directly dependent on the lighting or illumination level around said person. The activity signal may for example comprise at least one acceleration signal indicating a movement of the person. Additionally or alternatively it may comprise a physiological signal of the person, for example the heart rate, the blood pressure, or the body temperature.

The aforementioned parameters can be provided if the apparatus comprises an acceleration sensor and/or a physiological parameter sensor. Additionally or alternatively, the apparatus may comprise at least one light sensor for determining a lighting level, particularly the lighting level prevailing at the position of the person observed. All mentioned sensors may preferably be portable and carried or worn by the person.

According to another embodiment, a variable that is called "wakefulness variable" σ and that indicates a state of wakefulness or a state of sleep of the person may be determined from the current activity signal. The apparatus may comprise a "classification module" in which the determination of the wakefulness variable is executed. The wakefulness variable may substantially or exactly be binary, i.e. have—dependent on the current activity signal—only two possible values (indicating that the person is awake or asleep, respectively, at that particular time of the day.

The aforementioned classification module may particularly take a current lighting level into account, too. The contributions of the activity signal on the one hand side and the lighting level on the other hand side may for example be weighted by associated factors such that they can readily be adjusted according to the preferences of an operator. Setting the weighting factor of the lighting level to zero may for example provide for a wakefulness variable that depends on the activity signal but not on the lighting level. Similarly, any mixture of these two influences can be set by choosing appropriate weighting factors.

For determining the current value of the wakefulness variable, the classification module is assumed to take a current activity signal and optionally a current lighting level into account. According to a further development, the classification module may additionally take previous activity signals and/or previous lighting levels into account (wherein the term "previous" refers to time points prior then the current time point). The weight of previous lighting levels and/or activity signals will typically decrease with increasing temporal distance of the respective time points from the current time point. Taking also previous values into account helps to stabilize the wakefulness variable and to make it less dependent on transient values of the activity signal and/or the lighting level.

The classification module may optionally receive at least one user specific parameter as input, i.e. a parameter which depends on the person the circadian rhythm of which shall be estimated. Thus individual characteristics of this person can be taken into account. Different persons will for example typically have different baselines of activity such that one and the same activity signal may represent a state of wakefulness in one person but a state of sleep in another. The user specific parameter may particularly comprise a threshold to which the weighted sum of recent activity signals is compared and/or a threshold to which the weighted sum of recent lighting levels is compared (wherein "recent" comprises current and previous time points in the sense defined above).

A large variety of approaches and models can be used to estimate the model output x(t) based on the available information. According to one preferred embodiment, the model output is calculated based on a "driven van-der-Pol oscillator model". Driving inputs of this model may be influences (e.g. the lighting level) that may affect the circadian rhythm of the person. Without such influences, i.e. without driving inputs, the oscillator model typically represents the oscillating behavior of the circadian rhythm that can be observed in experiments with persons in isolated environments.

The aforementioned driven oscillator model may particularly comprise at least one driving term that is determined based on the current lighting level. Thus the influence of external lighting on the circadian rhythm of the person can be integrated into the model.

Additionally or alternatively, the driven oscillator model may comprise a driving term that is determined based on the current activity signal. Thus deviations of the actual circadian rhythm from the predicted one, which reveal themselves in the activity signal, can be taken into account.

The driven oscillator model may particularly be calculated based on the following differential equation $$\frac{d^2}{dt}x(t) - \mu \cdot (1-4x^2)\frac{d}{dt}x(t) + \left(\frac{2\pi}{\tau}\right)^2 x(t) = \frac{d}{dt}(B(t)+N(t)) \quad (1)$$

In this equation, μ and τ are given parameters and B(t) and N(t) are driving terms.

In a further development of the embodiment in which a driven oscillator model with the driving term N is used, said non-photic driving term may be determined based on the above mentioned wakefulness variable σ. The current activity signal is hence first transformed into the wakefulness variable σ which is then integrated into the driven oscillator model via a driving term. As the wakefulness variable is typically binary, this approach substantially results in a binary influence of the activity signal on the model output.

The driving term of the driven oscillator model may particularly depend on the model output itself. Hence external influences can be weighted differently depending on the current circadian state the model has estimated.

The driving term may particularly be zero or at least negligible at times that are substantially distant from the middle of the main sleep interval of the person. As the main sleep interval is indicated by the model output x(t) (if the estimation is correct), such a temporal concentration of the driving term can be achieved by making it dependent on the model output itself (as proposed in the previous paragraph).

The estimated model output can be used and be further processed for many different purposes. The apparatus may for example display the current model output x(t) and hence indicate the circadian rhythm to the monitored person such that deviations of the circadian rhythm from a target behavior can be detected and suitable counter-measures (e.g. changing the illumination) can be taken.

One parameter of interest that is often calculated from a circadian rhythm is abbreviated "CBTmin" and corresponds to the time at which a minimum core body temperature occurs. The CBTmin value may particularly be determined as the time for which a minimum output signal x(t) is estimated plus an offset.

In the aforementioned case the driving term N may particularly be proportional to a given gain factor, wherein the mentioned offset depends on said gain factor. Most preferably, the associated driving term is one that is based on the wakefulness variable. The dependence of the offset on the gain factor may for example be linear. It turns out that such a dependence considerably improves the predictions for the CBTmin value.

The described methods will typically be realized with the help of a computing device, e.g. a microprocessor or an FPGA in the associated apparatus. Accordingly, the present invention further includes a computer program product which provides the functionality of any of the methods according to the present invention when executed on a computing device.

Further, the present invention includes a data carrier, for example a floppy disk, a hard disk, an EPROM, a compact disc (CD-ROM), a digital versatile disc (DVD), or a USB stick which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

It shall be understood that the apparatus of claim 1, the system of claim 9, the method of claim 12, and the computer program of claim 15 have similar and/or identical preferred embodiments as defined in the dependent claims.

It shall be understood that a preferred embodiment of the invention can also be any combination of the dependent claims or above embodiments with the respective independent claim.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

A correct alignment of the circadian phase of a subject with the external time of his/her environment is of high importance. When the internal biological time of a subject is misaligned with the external "social" time, a number of symptoms are likely to occur, including phase advanced or delayed sleep disorders, jet-lag problems, or the so-called Seasonal Affective Disorder (SAD). When the circadian rhythms are chronically misaligned (e.g. in the case of shift-workers) the subject may suffer from reduced alertness or cognitive deficits up to more severe health problems implying a higher risk for cardiac failure and some hormonal cancers. Therefore, being able to reliably estimate the circadian phase of a subject is important not only for diagnostic purposes but also for the planning of appropriate counter-measures (e.g. light therapy or exogenous melatonin intake) to restore a proper entrainment of the subject with the external "Zeitgebers" as they act in daily life.

A non-photic extension to a light-based HCP model (HCP=Human Circadian Pacemaker) has been described in literature (M. A. St-Hilaire, E. B. Klerman, Sat Bir Khalsa, K. P. Wright Jr., C. A. Czeisler and R. E. Kronauer, "Addition of a non-photic component to a light-based mathematical model of the Human Circadian Pacemaker", Journal of Theoretical Biology, Vol. 247, pp. 583-599, 2007; this article is incorporated into the present text by reference). This model relies on a prior segmentation of the recorded data in terms of daily sleep and wake intervals and requires non-trivial computational steps that are incompatible with an "on-line" processing in real-time. Indeed, independently of CPU and memory costs, the daily sleep interval of a subject can only be determined with certainty after the wake-up time has been identified in the next morning, which imposes a delay of several hours. This approach is therefore only applicable in "off-line" mode.

In view of the above it is desirable to provide continuously circadian phase estimations of a subject with improved accuracy. According to an embodiment proposed here, this aim is achieved by taking the sleep/wake cycle explicitly into account (preferably in conjunction with the light exposure), based on a mathematical model of the human circadian pacemaker (e.g. Kronauer R. E., Forger D. B. and Jewett M. E., "Quantifying Human Circadian Pacemaker Response to brief, extended and repeated light stimuli over the photopic range" in J. Biological Rhythms, Vol. 14(6), pp. 501-516, 1999; this article is incorporated into the present text by reference). One aspect of the present consists in the incremental integration over time of a non-photic component, based on the concept of "rest and darkness" status, which is derived from the most recent activity and light measurements acquired by a sensing device. This enables a time-synchronous processing of each epoch of recorded data with no further delay.

Besides leading to a "left-to-right" on-line formulation of the processing algorithm, this method is also able to deal with fragmented sleep episodes or even with afternoon naps if the darkness requirement is relaxed. Additional constraints related to the wake maintenance zone, where sleep is unlikely, or other restrictions depending on either local or internal biological times, can be easily integrated in this framework. The method described in more details below thus enables an on-line integration at low computational cost of a non-photic component into the HCP model, based on an incremental processing of the sleep/wake cycle contributions to the circadian phase.

Figure 1:
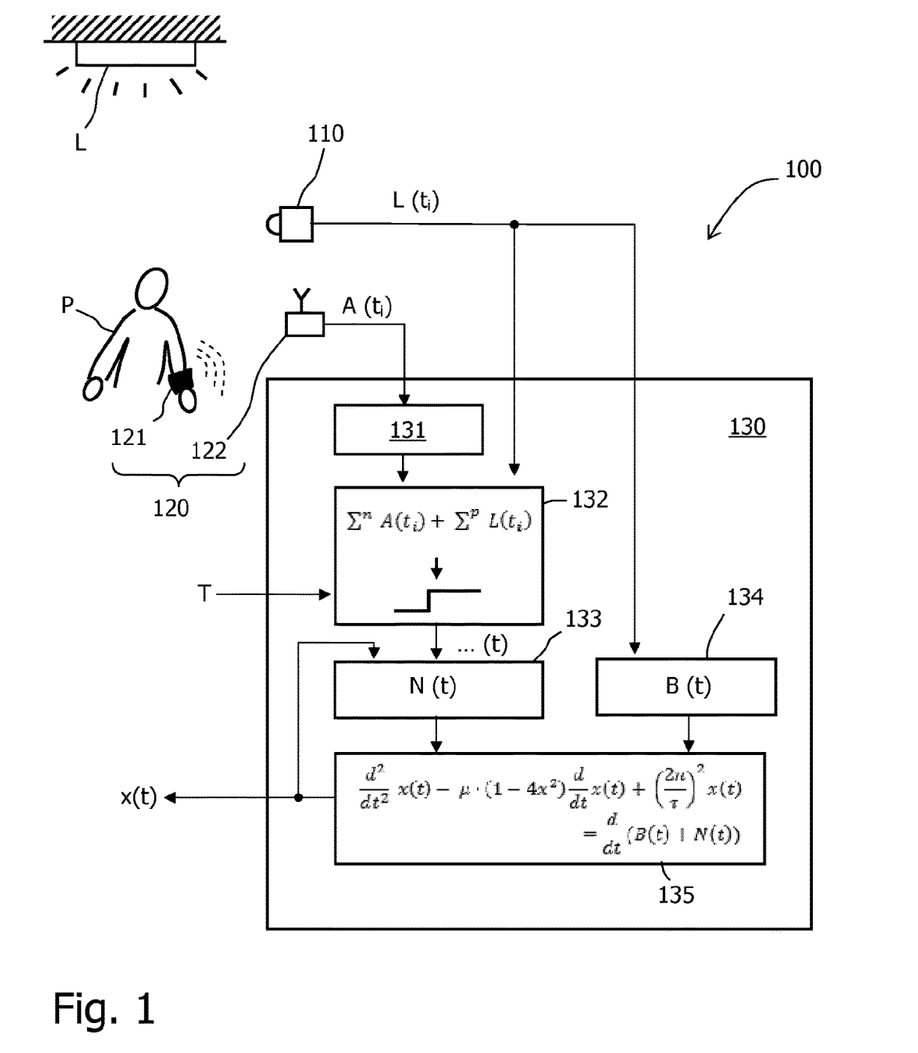
FIG. 1 shows schematically an apparatus according to an embodiment of the present invention for estimating a model output describing a circadian rhythm of a person.

FIG. 1 schematically illustrates an apparatus 100 that is designed according to be above general principles. The apparatus 100 is intended for estimating a "model output" x(t) which describes the circadian rhythm of a person P under observation.

As measurement or sensing equipment, the apparatus 100 comprises a light sensor 110 by which the lighting level $L(t_i)$ prevailing at the position of the person P can be measured. Though a stationary light sensor 110 is shown, this sensor may preferably be a device carried by the person P or integrated in a wrist device or worn as a pendent. The lighting may for example be generated by artificial lamps L of the surrounding room. In a further development of the approach, which is not described in more detail here, the lighting level may optionally be controlled based on the estimated model output x(t) and given targets for the circadian rhythm of the person. The light sensor 110 provides a corresponding lighting level signal $L(t_i)$, each time $t_i$ a measurement is made.

Furthermore, the apparatus 100 comprises at least one sensor 120 for determining an activity signal $A(t_i)$ indicating the activity of the person P at time $t_i$. Such a sensor 120 may for example comprise a component 121 that is worn by the person P and that transmits its measurement signals wirelessly to a receiver 122. The wearable component 121 may for example comprise an accelerometer for detecting movements of the person and/or sensors for physiological parameters such as heart rate, blood pressure or body temperature. Additionally or alternatively, the apparatus may comprise stationary activity sensors such as motion detectors (not shown).

The apparatus 100 further comprises a processor 130 which may for example be integrated into a stationary device (e.g. a personal computer) or a portable device such as a smart phone or a tablet computer. The processor 130 can also be a server which receives data from the sensors over a network and returns the results to the user again over the network. The processor 130 comprises several modules which are indicated as boxes in the drawing and which may be realized by dedicated hardware and/or by specific software (sub-) routines. In particular, the processor 130 comprises the following modules:

An "input module" 131 at which the activity signals $A(t_i)$ arrive and may optionally be preprocessed, e.g. by filtering, amplification and/or intermediate storage.

A "classification module" 132 which receives the current activity signal $A(t_i)$ from the input module 131 and, optionally, the current lighting level signal $L(t_i)$. Furthermore, the classification module receives external inputs T that can be set or adjusted by an operator, for example by a physician who monitors the measurements. The output of the classification module is a "wakefulness signal" σ(t). As will be explained in more detail below, the wakefulness signal σ(t) is calculated in the classification module 132 in two steps, namely by (i) calculating a score $RnD_{score}$ as a weighted sum of actual and previous values of the activity signal $A(t_i)$ and, optionally, the lighting levels $L(t_i)$, and (ii) by comparing this score $RnD_{score}$ to at least one threshold T to determine if the weighted data correspond to a state of wakefulness or a state of sleep. The result of this determination is encoded in the wakefulness variable σ(t).

A "first driving term calculation module" 133 in which the aforementioned wakefulness signal σ(t) and the current value x(t) of the model output are used to determine a first driving term N(t) that represents non-photic influences.

A "second driving term calculation module" 134 in which a second driving term B(t) is determined from the measured lighting levels $L(t_i)$.

A "simulation module" 135 in which a driven oscillator model is used to determine the model output x(t) based on the external driving terms N(t) and B(t) that are provided by the respective modules 133 and 134.

The described embodiment of the invention preferably applies digital measurements of activity and light-intensity levels acquired continuously, for example by a portable device (e.g. a wrist-watch or an actigraphy monitor). The data samples {$A(t_i)$, $L(t_i)$}, called "epochs", are acquired typically once per minute (at a rate ranging in [0.008, 0.067] Hz) and are processed in the processor 130 by an embedded software program implementing an algorithm comprising two main steps:

The first step is executed in the classification module 132 and comprises the classification of an incoming epoch of data in one of two possible states based on the concept of "rest and darkness". If the activity and light-intensity levels are above a threshold, the current epoch is tagged as "awake and active", whereas a low activity level observed in dim or no light is tagged as "at rest". Depending on the chosen setup, the classifier may be applied over activity levels only, or over both the activity and light levels, the information brought by the light-intensity having the potential of leading to more reliable decisions. In any case, the classifier applies on a small number of samples drawn from the recent past up to the current time with no use of data beyond the present time, for insuring a time-synchronous processing.

The second step is executed in the first driving term calculation module 133 and the simulation module 135. It concerns the immediate use of the classifier outputs in the pacemaker through a non-photic stimulus term driving the circadian oscillator.

An appropriate mathematical model for the simulation that provides the general HCP framework may for example be found in literature (St-Hilaire et al., Kronauer et al., cited above). The model is based on a limit-cycle oscillator of van der Pol type and can be described using the following 2nd-order differential equation, where external stimuli are introduced as a driving term Z(t) appearing on the right-hand side:

$$\frac{d^2}{dt^2}x(t) - \mu \cdot (1-4x^2)\frac{d}{dt}x(t) + \left(\frac{2\pi}{\tau}\right)^2 x(t) = \frac{d}{dt}(B(t)+N(t)) \quad (1)$$

Figure 2:
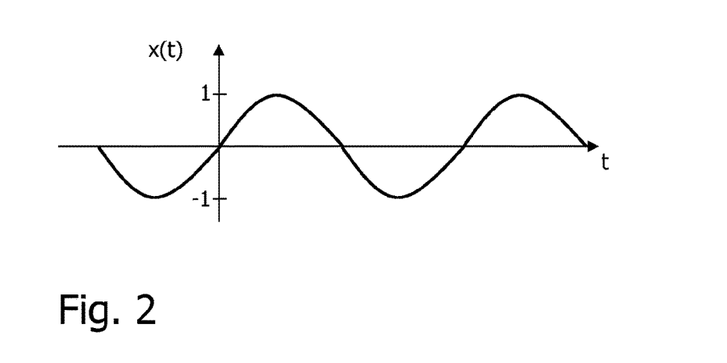
FIG. 2 schematically shows a model output that can be calculated with the apparatus of FIG. 1.

The dependent variable x varies analogously with the core body temperature (CBT) and oscillates over time t in a normalized range of [−1, +1]. This is schematically illustrated in FIG. 2. μ (0<μ<1) is the stiffness parameter and τ is the intrinsic period (about 24.2 hours). The forced "Zeitgeber" term Z(t) is the sum of a photic part B(t) depending on the light-intensity measurements and a non-photic part N(t) expressing the influence of the sleep/wake cycle on the circadian phase via the local epoch classifier.

The output σ($t_i$) of the binary classifier 132 may be set equal to "1" if the epoch status is "at rest" and to "0" if the epoch is tagged as "awake and active". The non-photic drive N(t) may be computed according to the following equation:

$$N(t) = \rho \cdot \left(\frac{1}{3} - \sigma(t)\right) \cdot (1 - \tanh(\varphi \cdot x(t))) \quad (2)$$

where ρ is the non-photic gain (0<ρ<0.2) and φ a parameter (1<φ<100).

Figure 3:
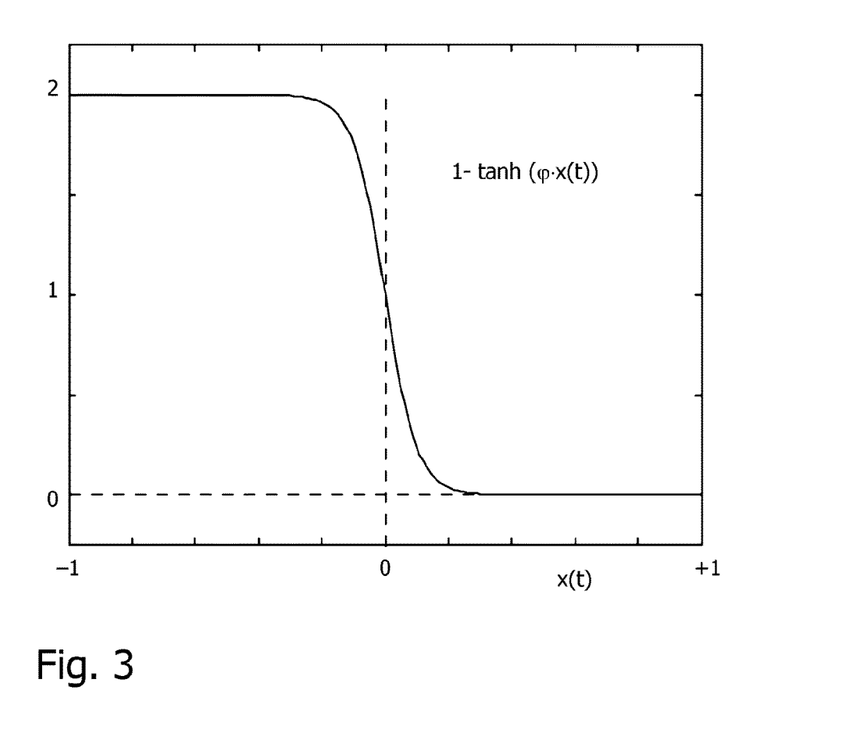
FIG. 3 schematically illustrates a factor appearing in the driving term of the oscillator model.

In equation (2), the first factor with σ(t) takes the value of −⅔ or +⅓ depending on the status of the epoch. The factor involving the hyperbolic tangent is illustrated in FIG. 3 and defines a circadian sensitivity modulation, which achieves a maximum value near the CBT nadir at x(t)~−1 and, for φ>>1, decreases rapidly to 0 for times distant from the singular point by a few hours. Thus, the sensitivity modulation emphasizes the non-photic influence in the vicinity of the CBTmin time, which occurs normally near the middle of the main sleep interval.

The photic term B(t) in equation (1) above is for example driven by the white-light illuminance values subjected to a non-linear compression and a retinal photo-transduction stage. These operations can all be evaluated time-synchronously without major difficulty, which completes the left-to-right numerical integration of the pacemaker model (1) and (2) and enables on-line circadian rhythm estimations. In other embodiments, B(t) may be driven by spectral irradiances of sub-parts of the visible spectrum, e.g. blue light. In general, the light input may be either white or colored, derived in the latter case for example from three light sensors providing the Red/Blue/Green irradiance measurements.

The next section explains how to build the classifier and how this non-photic extension is applied in practice, including an additive offset that depends on the non-photic gain ρ. This time-offset is added to the CBTmin predicted values to optimize the accuracy by reducing the estimation bias.

In a preferred embodiment, the algorithms described above are implemented as embedded software running on a small processor 130 integrated in a (portable) device providing continuous updates of the circadian phase of the subject P in ambulatory mode. Predicted values are typically updated every minute. The tagging of successive epochs in terms of rest and darkness status is done by a linear classifier meeting the requirements of time-synchronous processing at low computational costs.

Let $A(t_i)$ and $L(t_i)$ be respectively the activity and light-intensity levels at time $t_i$, i=1, 2, 3 . . . being the index of acquired epochs and I the current epoch index. The classifier score RnDscore is computed at current epoch I according to $$RnD_{score}(I) = w1 \cdot \sum_{i=0}^{n-1} \alpha(i) * A(t_{I-i}) + w2 \cdot \sum_{i=0}^{p-1} \beta(i) * L(t_{I-i}) \quad (3)$$

where w1 and w2 are the weights (≥0) for the respective contributions of activity and light to the classifier score, α(i) are the coefficients of the activity part involving the n past activity-counts, and β(i) are the coefficients of the photic part involving the p past light-intensities, up to I, the current incoming epoch. By setting w1=1 and w2=0, the classifier relies on activity levels only, whereas w1=0.5 and w2=0.5 would combine light and activity contributions in equal proportion. The coefficients α(i) and β(i) are normalized and are both summing to one. For example, α(0)=0.25, α(1)=0.5, α(2)=0.25 for n=3.

The decision rule for classifying an epoch in one specific state is based on the formula $$S = \text{sign}\{RnD_{score}(I) - w1 \cdot THR(\text{activity}) - w2 \cdot THR(\text{light})\} \quad (4)$$

where THR stands for a threshold related to either the activity or light levels. If the sign S evaluated in (4) is positive, the epoch is tagged as "awake and active" else it is considered to be "at rest". From (4), the wakefulness variable σ of equation (2) can be determined as $$\sigma(t) = (1-S)/2$$

For best performances, the threshold values THR(activity) and THR(light) can be made dependent on the subject P (the input of externally determined threshold values is symbolized by a letter "T" in FIG. 1). This may for example be based on the histogram of activity or light levels accumulated over the previous days of measurements. For example, starting from an initial value THR(activity)=$R_0$ derived from a typical value $R_0$ of the activity at rest, the activity threshold is updated on daily basis with the value of the 40% percentile of the observed activity counts so far. The same approach is applied for the light part of the classifier using the 20% percentile of the observed light intensities so far.

A further point concerns the definition of the predicted phase-marker associated to the daily timing of the CBT nadir, denoted as CBTmin, according to $$CBT_{min} = \text{argmin}_t(x) + \text{offset}(\rho) \quad (5),$$

where x is obtained as the solution of equation (1) above and the added offset is made dependent on the size of the non-photic gain ρ. It is proposed here to apply a monotonically decreasing offset such that the effects of the non-photic contribution to the predicted phase are optimized. Among other more complex possibilities, the following linear regression has shown especially effective for reducing the size of the bias in the circadian phase estimation:

$$\text{offset}(\rho) = 1.0 - 6.5 \cdot \rho \text{ (expressed in hours)} \quad (6).$$

The gain value ρ is usually set to 0.1, however, it can also be adapted to the specific chronotype characteristics of the subject. For ρ=0.1, the time offset is reduced to 0.35 hours.

The phase prediction accuracy has been evaluated using three statistical measures quantifying the similarity of the estimated values with reference DLMO (Dim Light Melatonin Offset) phase markers obtained from evening saliva sampling of the considered subjects. The standard deviation of the differences between DLMO and predicted phase values is a first index of group-performance, the Pearson correlation coefficient of both sequences provides a second index of group-performance and a 3rd index is the mean of the absolute difference of each individual pair of predicted and reference values.

When tested over a set of 81 subjects (excluding severe chronotype outliers) recorded in their unconstrained daily life over one week or more, the following results have been achieved:

| TEST-SET | NP-gain | STD-DEV | CORREL | Mean ABS-ERROR | Max ABS-ERROR |
|---|---|---|---|---|---|
| 81 subjects (41 females) | 0.0 | 0.596 H | 0.76 | 0.64 H | 1.73 H |
|  | 0.1 | 0.478 H | 0.84 | 0.40 H | 0.97 H |

Figures in the above table show a relative reduction of the standard deviation by 20%, a relative increase of the (Pearson) correlation coefficient by 11%, a relative reduction of the mean absolute-value of the errors by 37%, and a reduction of the maximum errors by 44%. This indicates the potential of the present technique for improving the phase prediction accuracy by means of an incremental contribution of the sleep/wake cycle in a circadian pacemaker.

In summary, an embodiment of a real-time integration of non-photic aspects of the sleep/wake cycle in a circadian pacemaker model and its application for achieving improved phase prediction accuracy has been described. The method is based on a local classifier of activity and light measurements in terms of rest and darkness status, and does not require a prior segmentation in sleep and wake intervals. The classifier output is combined with the main photic stimuli derived from light-sensing elements capturing the current illumination of the subject. This enables a time-synchronous processing of data, suited for mobile applications using limited hard-ware devices like actigraphy wrist-watches, and is meant for on-line estimations of the (human) circadian phase with enhanced precision.

The described approach can for instance be applied in relation to small actigraphy devices including light sensors. It can be applied in general context of chrono-medicine, including light therapy, with an emphasis on real-time management of circadian rhythm problems. More specifically, a possible application relates to products that are targeting people with Delayed Sleep Phase Disorder and chronic insomniacs. The solution presented here can contribute to higher accuracy circadian phase estimations in real-world, which can be used to provide recommendations and advices to the subject in real-time. One target population is made of people suffering from chronic insomnia (about one third of insomnia complaints are presumably related to circadian disorders) and also specific categories like shift workers. In the "lifestyle" sector, chrono-therapy may be regarded as a tool for improving alertness and cognitive performances at particular times of the day, to reduce Jet-Lag effects consecutive to trans-meridian travels and for alleviating typical symptoms related to weak forms of depression. Another field of possible applications relates to chrono-medicine, where the knowledge of the patient's circadian phase may be exploited to improve the efficiency of pharmaceutical drugs and minimizing their side effects, e.g. in cancer therapy.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The present invention relates to an apparatus and a method for estimating a model output describing a circadian rhythm of a person. In a preferred embodiment, a light sensor providing the photic exposure and an activity signal indicating the current level of activity of the person based on motion measurements (via an accelerometer) are used to calculate a binary wakefulness variable that indicates if the person is awake or sleeping. The wakefulness variable is then used to determine a driving term for a driven oscillator model which simulates the model output under the joint influence of light and activity.

The invention claimed is:

1. An apparatus for generating a model output at a first time describing a circadian rhythm of a person, said apparatus comprising:
   (a) an input module configured to:
      receive an activity signal and/or a lighting level signal, the activity signal being (i) indicative of a current level of activity of the person at the first time and (ii) based on activity level measurements, the lighting level signal being indicative of a lighting level at the first time at a location of the person;
   (b) a classification module configured to:
      (1) receive a threshold of the person;
      compare the threshold of the person to a weighted sum of recent activity signals and/or recent lighting level signals, the recent activity signals corresponding to activity signals taken prior in time to the first time, and the recent lighting level signals corresponding to lighting level signals taken prior in time to the first time; and
      (2) generate a wakefulness signal at the first time based on the comparison, the wakefulness signal being indicative of the person being awake or asleep at the first time;
   (c) a first calculation module configured to determine a non-photic driving term at the first time based on the wakefulness signal, the non-photic driving term representing a non-photic influence on the circadian rhythm; and
   (d) a simulation module configured to calculate in real time the current model output at the first time based on the non-photic driving term.

2. The apparatus according to claim 1, wherein the classification module is configured to generate the wakefulness signal based on the lighting level signal and the activity signal.

3. The apparatus according to claim 1, further comprising:
   a second calculation module configured to determine a photic driving term from the lighting level signal, the photic driving term representing a photic influence on the circadian rhythm, and
   wherein the simulation module is configured to calculate in real time the current model output at the first time based on the non-photic driving term and on the photic driving term.

4. The apparatus according to claim 3, wherein a classifier score is computed at a current epoch according to $$RnD_{score}(I) = w1 \cdot \sum_{i=0}^{n-1} \alpha(i) * A(t_{I-i}) + w2 \cdot \sum_{i=0}^{p-1} \beta(i) * L(t_{I-i})$$

where w1 and w2 correspond to predetermined first and second weights, where w1≥0 and w2≥0, where α(i) correspond to predetermined non-photic coefficients, and where β(i) correspond to predetermined photic coefficients, and where the current epoch corresponds to a current period in time.

5. The apparatus according to claim 1, wherein the classification module is configured to generate the wakefulness signal at the first time based on the recent activity signals and the recent lighting level signals.

6. The apparatus according to claim 5, wherein the classification module is configured to compare the threshold of the person to the weighted sum of the recent activity signals and the recent lighting level signals, wherein the classification module is further configured to generate a personal baseline of activity or lighting level for the person.

7. The apparatus according to claim 1, wherein the current model output is calculated based on a driven van-der-Pol oscillator model.

8. The apparatus according to claim 7, wherein the non-photic driving term is proportional to a gain factor, and wherein a time at which a minimum core body temperature of the person occurs is determined as the time for which a minimum current output signal is generated plus an offset, wherein the offset depends on the gain factor, wherein the offset is expressed as a–b·ρ, where a and b are constant, and where ρ corresponds to the gain factor.

9. A system for generating a model output $x(t_i)$ at a first time describing a circadian rhythm of a person, said system comprising:
(a) at least one sensor for determining an activity signal at a first time indicating the activity of the person at the first time; and
(b) an apparatus for generating a model output at a first time describing a circadian rhythm of a person, said apparatus comprising:
(1) an input module configured to receive an activity signal and/or a lighting level signal, the activity signal being (i) indicative of a current level of activity of the person at the first time and (ii) based on activity level measurements, the lighting level signal being indicative of a lighting level at the first time at a location of the person:
(2) a classification module configured to:
(i) receive a threshold of the person; compare the threshold of the person to a weighted sum of recent activity signals and/or recent lighting level signals, the recent activity signals corresponding to activity signals taken prior in time to the first time, and the recent lighting level signals corresponding to lighting level signals taken prior in time to the first time; and
(ii) generate a wakefulness signal at the first time based on the comparison, the wakefulness signal being indicative of the person being awake or asleep at the first time;
(3) a first calculation module configured to determine a non-photic driving term at the first time based on the wakefulness signal, the non-photic driving term representing a non-photic influence on the circadian rhythm; and
(4) a simulation module configured to calculate in real time the current model output at the first time based on the non-photic driving term.

10. The system according to claim 9, wherein the at least one sensor is an acceleration sensor or a physiological parameter sensor, wherein the physiological parameter sensor is a heart rate sensor, a blood pressure sensor, or a body temperature sensor.

11. The system according to claim 9, further comprising a sensor for determining a lighting level signal at the position of the person at the first time.

12. A method for generating a model output at a first time, the model output describing a circadian rhythm of a person, the method comprising:
receiving an activity signal and/or a lighting level signal, the activity signal being (i) indicative of a current level of activity of the person at the first time and (ii) based on activity level measurements, the lighting level signal being indicative of a lighting level at the first time at a location of the person;
receiving a threshold of the person;
comparing the threshold of the person to a weighted sum of recent activity signals and/or recent lighting level signals, the recent activity signals corresponding to activity signals taken prior in time to the first time, and the recent lighting level signals corresponding to lighting level signals taken prior in time to the first time;
generating a wakefulness signal at the first time based on the comparison, the wakefulness signal being indicative of the person being awake or asleep at the first time;
determining a non-photic driving term at the first time based on the wakefulness signal, the non-photic driving term representing a non-photic influence on the circadian rhythm; and
calculating in real time the current model output based on the non-photic driving term.

13. The method according to claim 12, further comprising:
determining a photic driving term from the lighting level signal; and
calculating in real time the current model output at the first time based on the non-photic driving term and on the photic driving term.

14. The method according to claim 12, wherein the wakefulness signal is calculated by:
(i) calculating a score (RnDscore) as the weighted sum of current and past activity signals and/or of current and past lighting level signals; and
(ii) comparing the score (RnDscore) to the threshold.

15. A non-transitory, machine-readable media storing instructions that, when executed by one or more physical processors, effectuate operations comprising:
receiving an activity signal and/or a lighting level signal, the activity signal being (i) indicative of a current level of activity of a person at a first time and (ii) based on activity level measurements, the lighting level signal being indicative of a lighting level at the first time at a location of the person;
receiving a threshold of the person;
comparing the threshold of the person to a weighted sum of recent activity signals and/or recent lighting level signals, the recent activity signals corresponding to activity signals taken prior in time to the first time, and the recent lighting level signals corresponding to lighting level signals taken prior in time to the first time; and
generating a wakefulness signal at the first time based on the comparison, the wakefulness signal being indicative of the person being awake or asleep at the first time;

determining a non-photic driving term at the first time based on the wakefulness signal, the non-photic driving term representing a non-photic influence on a circadian rhythm of the person; and
calculating in real time a current model output at the first time based on the non-photic driving term.

\* \* \* \* \*